United States Patent [19]

Leblanc et al.

[11] 4,222,261
[45] Sep. 16, 1980

[54] DEVICE FOR MEASURING THE WATER CONTENT OF A MOVING GAS

[75] Inventors: Michel Leblanc, Roncq; Jacques Lanérés, Bondues; Jean Perrin, La Chapelle d'Armentieres, all of France

[73] Assignees: Institut Textile de France; Michel Leblanc; Agence Nationale de Valorisation de la Recherche (ANVAR), all of France

[21] Appl. No.: 3,752
[22] Filed: Jan. 15, 1979

[30] Foreign Application Priority Data

Jan. 16, 1978 [FR] France .................. 78 01123

[51] Int. Cl.³ .......................... G01N 25/62
[52] U.S. Cl. .......................... 73/29; 73/338
[58] Field of Search ............ 73/29, 338.6, 338, 77

[56] References Cited

U.S. PATENT DOCUMENTS

| | | | |
|---|---|---|---|
| 1,620,864 | 3/1927 | Benesh | 73/29 |
| 1,890,565 | 12/1932 | Austin | 73/338 X |
| 1,894,172 | 1/1933 | Guthrie et al. | 73/29 |
| 2,845,790 | 8/1958 | Eddy | 73/29 |
| 2,915,898 | 12/1959 | Van Luik, Jr. | 73/29 X |
| 2,926,521 | 3/1960 | Booth | 73/29 |
| 3,603,135 | 9/1971 | Kawaguchi | 73/29 |
| 3,890,828 | 6/1975 | Pleva | 73/29 |
| 4,129,250 | 12/1978 | Chaikin et al. | 73/77 X |

FOREIGN PATENT DOCUMENTS 808495  7/1951  Fed. Rep. of Germany .............. 73/29

Primary Examiner—Gerald Goldberg
Assistant Examiner—Joseph W. Roskos
Attorney, Agent, or Firm—Lewis H. Eslinger

[57] ABSTRACT

A psychrometer or pick-up for measuring the content of water in a gas flow comprises a first sensor or probe for measuring the dry temperature of the gas and is arranged directly in the flow of gas, a second sensor or probe for measuring the wet temperature of the gas and is surrounded by a sheath of a material capable of absorbing a volatile liquid, the second sensor or probe with its sheath also being arranged in the flow of gas, a pair of screens mounted on opposite sides of the second sensor and the sheath for protecting the sheath against thermal radiation, and a wetting device, preferably formed by a dosing pump connected to a nozzle, for injecting successive doses of a predetermined amount of the volatile liquid directly into the interior of the sheath and onto the screens to prevent excessive and insufficient moistening of the sheath and the screens.

7 Claims, 5 Drawing Figures

DEVICE FOR MEASURING THE WATER CONTENT OF A MOVING GAS

The present invention relates to a psychrometer or pick-up for measurement of the water content of a gas in motion, of the type including means of support upon which are mounted: a temperature measurement probe called the "dry" one, located directly in the flow of gas, a temperature measurement probe called the "wet" one, surrounded by a sheath—or wick—of material suitable for being soaked in a volatile liquid, this sheathed wet probe being likewise located in the said flow of gas, and means called the wetting means for feeding this sheath with volatile liquid.

In known pick-ups of this type the measurement by the wet probe is falsified by the thermal radiation from the walls in its vicinity. This thermal radiation increases very rapidly with the temperature of these walls which is that of the flow of gas of which it is required to measure the water content.

Now, measurement of humidity at relatively high temperatures such as 100° C. or more, appear more and more necessary to industry which for the moment has available systems based on the velocity of sound in air or the employment of a lithium chloride probe and very often by sampling technique.

The object of the present invention is in particular to eliminate the disadvantages inherent in these known devices, to enable a measurement to be carried out directly in the existing pipework, this being done with satisfactory accuracy and over a wide field of temperatures extending to temperatures higher than 100° C.

Its object likewise is, thanks to means put into effect, that of delivering information expressed directly in grammes of water per kilogramme of dry air over a field extending by several degrees to at least 250° C.

These objects are achieved in accordance with the invention by the fact that on opposite sides of the wet probe equipped with its sheath are provided two screens for protection against thermal radiations and in that wetting means are provided for moistening each of the said screens with a volatile liquid.

Thus the radiation from the walls is practicaly eliminated by the presence of the screens which are at the same temperature as the wick. Hence there is no temperature gradient between the wet probe and its walls. In order to keep the screens at a low temperature the psychrometric effect is employed. For this reason they consist of matter which retains water. In accordance with one embodiment of the invention these screens are of fritted glass.

The screens are advantageously produced from material suitable for being soaked in liquid.

The means of wetting the screens and the sheath advantageously comprise one single source of liquid under pressure.

The means of wetting the sheath advantageously consist of means which inject the liquid directly into the sheath and discontinously according to at least one injection of a certain amount of liquid.

The means of wetting the sheath are advantageously means which inject the liquid into the sheath discontinuously in a number of successive injections, each of a predetermined amount of liquid and taking into account the amount of liquid injected at each injection, the intervals between each injection of liquid are sufficiently short for the sheath never to be completely dry, but are sufficiently long for the level stretch of psychrometric temperature to be reached.

Thus in the pick-up in accordance with the invention the feed of water to the wick is discontinuous. The humidification is controlled by volume and outside of the phase of injection of water there is no contact between the wet probe and the water feeding device.

The means of wetting the sheath are advantageously means which emit the liquid in the form of at least one jet leaving an outlet orifice and directed towards a receiving and guide wall provided at the level of the top end of the sheath and spaced from the said outlet orifice so as not to intersect the vertical through the latter.

Advantageously the sheath is tubular, it is inclined with respect to the horizontal and it exhibits at its top end an opening which receives the liquid supplied by the wetting means.

The axis of the sheath is advantageously inclined at 20° to 60° with respect to the horizontal.

Thus in the pick-up in accordance with the invention the water contained in the pipework subjected to high temperature can evaporate without disadvantage; the volume which evaporates is in general a fraction of a cubic centimeter and thanks to that and to the arrangement which has just been specified, this vapour leaving the said outlet orifice cannot create any micro-climate capable of influencing the temperature of the wet probe nor enter into direct contact with the wet probe.

At the time of the injection or succeeding humidification, the arrival of cold water external to the pick-up causes lowering of the temperature of the pipework. The water is injected in the liquid phase and under pressure towards the wet probe which will set itself at the psychrometric temperature a certain time after this operation.

The measurement device in accordance with the invention essentially constitutes a psychrometric technique which is very clearly improved with respect to the use of a simple dry thermometer and wet thermometer. Moreover this device can deliver linear information which can be employed for purposes of indication, recording or regulation.

This pick-up comprises in accordance with one embodiment: a dry thermometer no. 1, a dry thermometer no. 2 and a wet thermometer. These members are completed:

- by means of cyclic injection of water which inject the water through the interior of the hygroscopic element called conventionally the wick;
- by means of protection against the vapour phases, consisting of an inclination of 20° to 60° of the axis of the wet wick with respect to the horizontal and by a certain distance between the water injector and the wick;
- by means of protection of the wet pick-up consisting of anti-thermal radiation screens;
- by an electronic operating circuit which delivers the water content expressed in grammes of water per kilogramme of dry air.

This pick-up has especially as its advantages:
easy interchangeability of the wick;
interchangeability of the wet pick-up from the outside;
reduced consumption of water;
satisfactory behaviour at temperatures of the pick-up up to 250° C.

The sheath is advantageously mounted on a sheath-carrier comprising a first perforated tubular portion surrounding the sheath and supporting it by its top end and a second portion supporting the first portion, this second portion being mounted on the support means so as to be detachable from the outside of channelling means in which the said pick-up is located.

Thus the wick mounted on a wick-carrier is accessible from the outside of the pick-up and its replacement may be performed in a few seconds.

The pick-up advantageously includes in addition a memory capable of receiving information called outlet information worked out from temperature information supplied by the measurement probes, and a control device which receives the wet temperature signal supplied by the wet probe, works out the differential with respect to time of this wet temperature signal and supplies to the said memory an outlet information recording command as soon as the said differential become less than a predetermined value.

Other characteristics and advantages of the invention will be better understood from the description which is to follow of an embodiment and by referring to the attached drawings in which.

Figure 1:
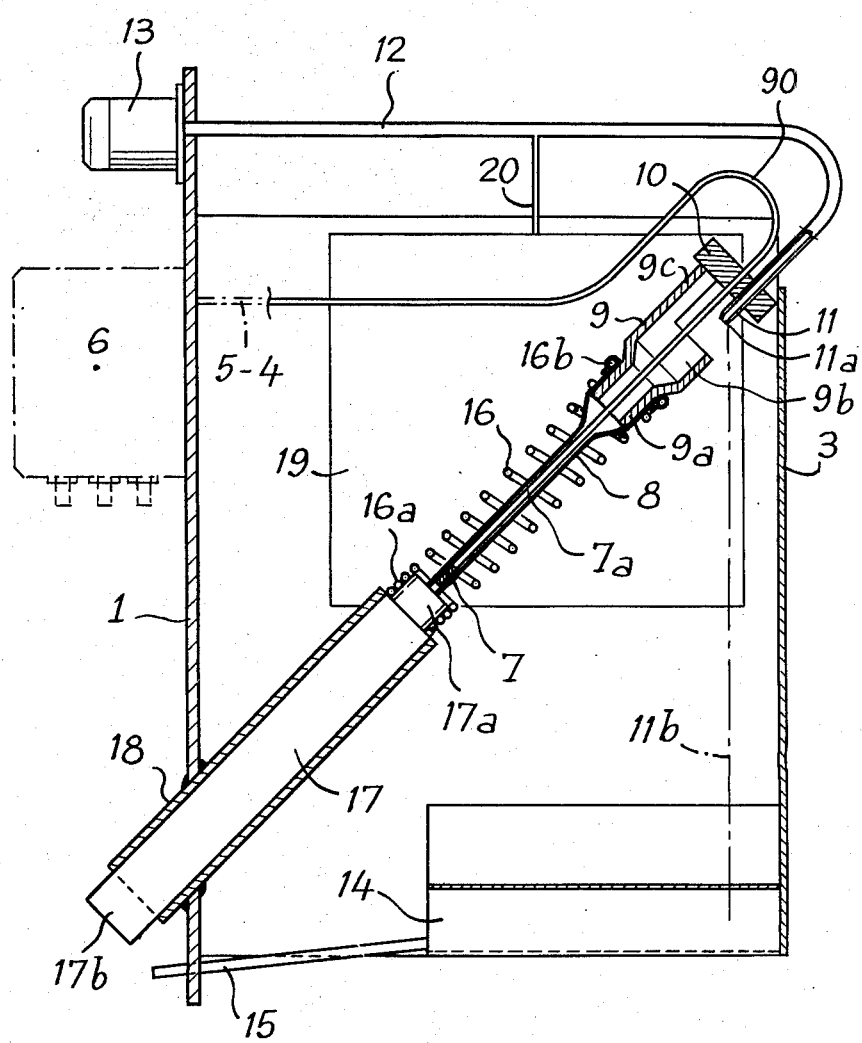
FIG. 1 is a diagrammatic elevation and vertical section along I—I in FIG. 2, of the device in accordance with one embodiment of the invention.
Figure 2:
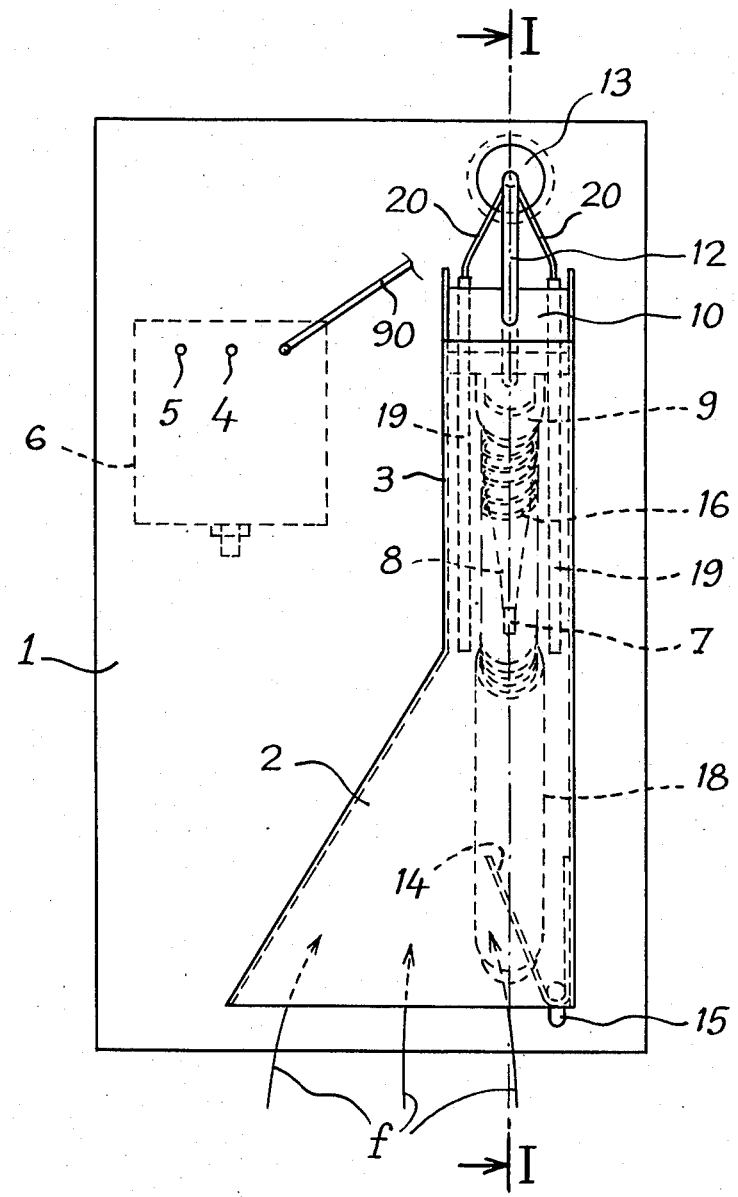
FIG. 2 is a profile of the device represented in FIG. 1.

The measurement device represented in FIGS. 1 and 2 comprises a supporting plate 1 arranged vertically upon which is mounted a vertical duct intended to channel a flow of gas—for example, air—of which it is required to measure the content of water. This duct comprises from the bottom upwards a convergent section 2 followed by a section of constant area 3. Driving means (not shown) are provided in order that a flow of gas entering through the bottom (arrow f) flows vertically from the bottom upwards in this duct 2,3.

Inside this duct are arranged two probes for measurement of so-called dry temperature. These probes which for greater clarity have not been shown in FIG. 1 are directly in contact with the flow of gas passing through the duct 2,3 and they are connected each by an electric cable respectively 4,5 to a junction box 6 mounted on the supporting plate 1. These probes consist each, for example, of a platinum resistor.

A pick-up of so-called wet temperature is placed in the duct 2,3 and preferably at the output from the convergent portion 2.

This pick-up comprises a temperature probe 7 surrounded contiguously by a tubular sheath—or wick—8 produced from a material suitable for being impregnated with water such as a material of natural or synthetic textile fibres or more generally a mineral or organic material having the faculty of holding water.

The probe 7 consisting, for example, of a platinum resistor is located at the free end of a rigid rod 7a containing the conductors for connection to the probe 7; these conductors leave the rod 7a in the form of a connecting cable 90 connected at its other end to the junction box 6.

In known devices the wick of the wet pick-up is fed with water continuously by means of a volume of water into which one end of this wick dips. Thus these known devices cannot operate at temperatures higher than 100° C. because at these temperatures the water in the said volume starts to boil, creating a micro-climate saturated with moisture and bringing about an excessive consumption of water.

In order to correct that, the tubular wick 8 is fed with water discontinuously by the following means: the wick 8 is arranged non-horizontally, it extends substantially above the probe 7 and it is threaded at its top end into a tubular connector 9a of a hollow part forming a funnel 9 which by way of an arm 9c is supported by a wall 10 through which passes the rod 7a. The wall 10 is attached to the walls of the section of duct 3 and it is likewise passed through by a tube forming a nozzle 11 directed towards the chamber 9b inside the part 9. The tube 11 is connected by pipework 12 to the output from a proportioner pump or a timed volumetric pump 13. By putting the pump 13 into service one causes through the nozzle 11 in the form of a water jet directed towards the connector 9a and hence towards the wick 8, the emission of a predetermined amount of water which is thus directly injected inside the wick 8. The non-horizontal arrangement of the wick 8 enables the placing in reserve of a certain amount of water in the space existing between this wick and the rod 7a terminating in the pick-up 7.

As may be seen in FIG. 1, the common axis of the wick 8 and the parts 7 and 7a is inclined at 45° with respect to the vertical. This slope enables both the putting into reserve of a certain amount of water in the space existing between the wick 8 and the rod 7a or the probe 7 and good contact between the wick 8 and the streams of the flow of ascending gas.

As is shown in FIG. 1, the free end 11a of the nozzle 11 is sufficiently far from the part 9 for the latter not to intersect the vertical 11b through the said end 11a. Thus, for the water leaving the nozzle 11 to penetrate into the part 9 and into the sheath 8 it is necessary for this water to be thrown in the form of a sufficiently powerful jet leaving the said nozzle 11.

Vertically below the wick 8 is a V-section trough 14 intended for recovering the excess water which may trickle from the wick 8. The trough 14 is sloped downwards in the direction of the inlet aperture to exhaust pipework for the excess water 15.

The wick 8 is mounted on a wick-carrier comprising a coil of metal wire or round rod 16 having non-contiguous turns except at its bottom end 16a which is screwed onto a threaded cylindrical projection 17a from a cylindrical part 17 which engages with slight friction in a sheath—or tube—18 attached to the support plate 1. The wick 8 is attached at its top end by, for example, sewing onto the top turn 16b of the coil 16. The part 17 projects at its bottom end from the adjacent end of the sheath 18 so that outside the said sheath there exists an end to catch hold of, 17b, by means of which the wick-carrier 16, 17 and the wick 8 which is mounted on it can be withdrawn.

Of course the part 9 might be replaced by an extension of the sheath 8 opened out upwards; in this case the free edge of this extension would be attached to the top end turn of the coil 16 and the latter might exhibit at its top end a shape opening out upwards.

In known devices the wet temperature measured by the so-called wet probe is falsified by the effect of thermal radiation from the walls of the duct through which the flow of gas is passing.

In order to correct this disadvantage in the device in accordance with the present invention, a plane screen 19 is arranged on each of the opposite sides of the wet probe 7,8. The screens 19 are panels parallel with one another consisting of a porous substance of high capillarity and they are each humidified at the same time as the wick 8 by means of two pipes 20 tapped from the piping 12. The two screens 19 are located in the path of the flow of gas passing through the duct 2,3 and are arranged vertically.

Figure 3:
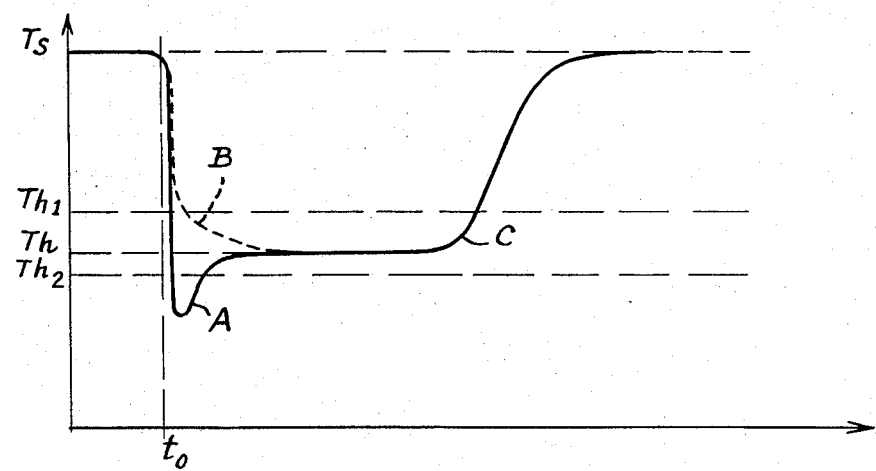
FIG. 3 is a graph as a function of time, of the temperature measured by the so-called wet probe for one single injection of water into the wick.

FIG. 3 shows the development as a function of time, of the so-called wet temperature measured by the probe 7 when only one single injection of water has been effected into the wick 8.

This injection of water is carried out at the time $t_o$. This injection causes a drop in the wet temperature from the value $T_s$ equal to the so-called dry temperature measured by the two other probes down to a temperature substantially equal to that of the injected water. Depending upon whether this water temperature is lower or higher than that ($T_h$) of the psychrometric stage, this decrease in temperature will occur along the curve B or along the curve A but this wet temperature will in both cases reach the same value $T_h$ at the end of a certain time. Then if there is no new injection of water this temperature will rise again until reaching the value $T_s$.

Figure 4:
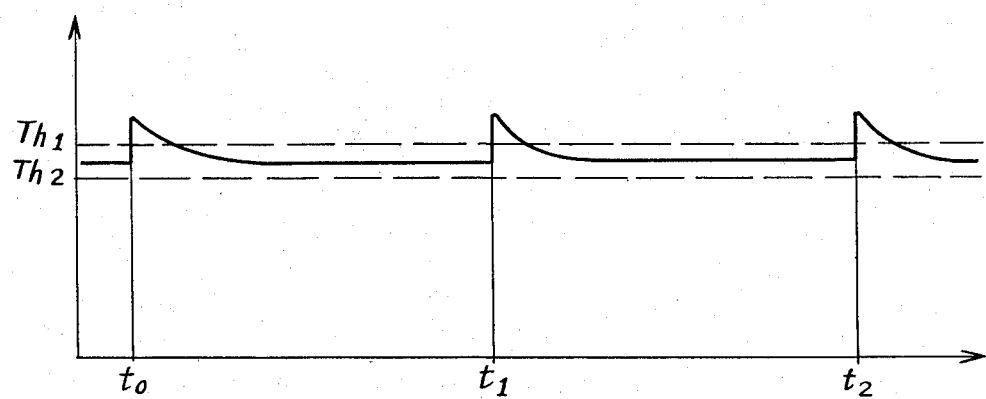
FIG. 4 is a graph similar to that as FIG. 2 but obtained in the case of a discontinuous and periodic feed of water to the wick.

In accordance with the present invention successive dryings undergone by the wick 8 are avoided; for this purpose, as shown in FIG. 4, water is fed to the wick 8 again before the wet temperature measured by the probe 7 starts the arc C to rise again (FIG. 3).

Figure 5:
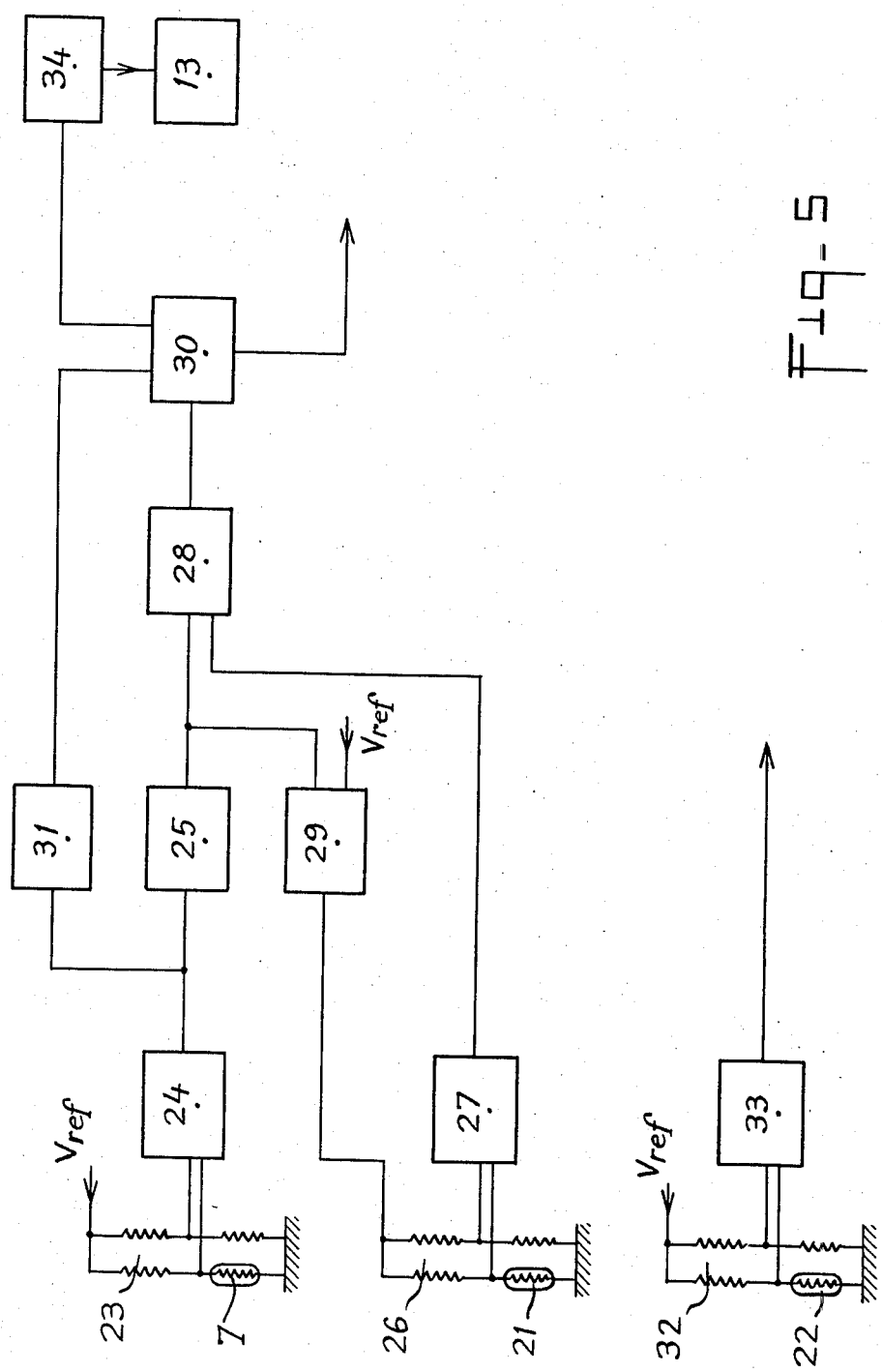
FIG. 5 is a block diagram of the electronic processing circuit employed in the device in accordance with one embodiment of the invention.

The wet probe 7 as well as the two dry probes respectively 21 and 22 are associated with a processing electronic circuit which supplies directly the water content of the gas in grammes of water per kilogramme of dry gas. The circuit represented in FIG. 5 comprises a Wheatstone bridge 23 fed by a steady voltage $V_{ref}$, associated with the probe 7. The signal supplied by the bridge 23 is amplified at 24 and then processed in a so-called linearisation circuit 25 which transforms the signal s leaving the amplifier 24 into a signal f (s) such that f (s) is equal to the humidity content of the gas in grammes of water per kilogramme of dry gas, corresponding with the wet temperature of the probe 7 and with a dry temperature taken as reference. The circuit 25 may, for example, consist of an operational amplifier upon which is mounted a non-linear negative feedback.

Thus the signal f (s) supplied by the circuit 25 represents the true humidity content when the dry temperature measured by the probe 21 or the probe 22 is equal to the said dry reference temperature. In the contrary case the signal f (s) is corrected in the following fashion:

The probe 21 is mounted on a Wheatstone bridge 26 balanced at the said reference temperature. The output signal from the bridge 26 after amplification in 27 is applied to one input to a summation circuit 28 which receives at its other input the signal f (s) to be corrected. In order to increase the efficiency of the correction the supply voltage to the bridge 26 comprises in addition to a steady component $V_{ref}$ a component modulated as a function of the value of the signal f (s) supplied by the circuit 25. An adaptor circuit 29 receiving the signal f (s) and the voltage $V_{ref}$ supplies at its output the said modulated component.

A memory 30 collects the so-called output information present at the output from the circuit 28; this memory receives on behalf of a suitable control circuit 31 a command to take into account the said information supplied by the circuit 28. The circuit 31 receives the output signal from the amplifier 24. This circuit 31 may be designed so that the output information is retained by the memory 30 only when the following conditions are satisfied:

the wet temperature must lie between two limiting values $T_{h1}$ and $T_{h2}$ (FIGS. 3 and 4). These values are, for example, 40° and 75° C. corresponding in the case of air to a humidity going up as far as 250 g of water per kilogramme of dry air for a dry temperature of 50° to 250° C.;

a certain time must have passed after the injection, this time being typically some tens of seconds;

the differential as a function of time, of the wet temperature must be less than a certain threshold.

The second dry temperature probe 22 supplies a measurement of dry temperature for checking or recording. This probe 22 is mounted like the probe 7 on a Wheatstone bridge 32 fed by a steady voltage $V_{ref}$. An amplifier 33 amplifies the output voltage from the bridge 32.

The proportioner pump 13 is triggered at suitable times by a circuit 34 which receives information supplied by the memory 30 or by the circuit 31. Thus the method of cyclic injection of water into the wick enables an amount of water to be supplied at a predetermined time which humidifies the wick 8 and the anti-radiation screens 19.

In accordance with one embodiment the humidification of the so-called wet probe:

is done through the inside of the wick 8 inclined at 45°;

is effected only if the water is injected at a sufficient pressure to clear a distance of about 10 mm between the water outlet mouthpiece 11 and the top end of the wick 8.

Under these conditions the humidification of the wick 8 is regular and it cannot be humidified by chance drops of water due either to steam or to expansions of the water inlet pipes.

As soon as the injection of water into the wick is completed the temporary phenomena of the development of temperature in the pipework 12,20 have no effect upon the wet probe even if this temperature clearly exceeds 100° C. At the following injection the volume of water proceeding from the outside will have as its consequence a lowering of the temperature of the pipework again and the humidification of the wick 8 and the screens 19. In sum, outside of injection times the wet probe is isolated from the water feed device. It may if it is located in a flow of air at a minimum speed of 2 meters per second, reach the psychrometric temperature.

The temperature reached by the wet probe at the time of the end of the humidification phase is illustrated by the diagram of FIG. 3.

The stage temperature $T_h$ may be influenced by the thermal radiation from the walls of the duct 23. It is in order to avoid this very troublesome phenomenon above all at temperatures higher than 100° C., that the anti-radiation screens 19 are put in place, which, swept by the same flow of air as the probe, have as their surface temperature the psychrometric temperature.

Hence this method eliminates the thermal radiation from the walls over a large solid angle.

We claim:

1. A psychrometer for measuring the water content in a flow of gas, comprising:
   support means;
   first sensor means mounted on said support means and located directly in said flow gas for measuring the dry temperature of said flow of gas;
   second sensor means mounted on said support means for measuring the wet temperature of said flow of gas;
   a sheath surrounding said second sensor means and also located in said flow of gas, said sheath being adapted to absorb a volatile liquid;
   a pair of screens mounted on opposite sides of said second sensor means and said sheath for protecting said sheath against thermal radiation; and
   means for wetting said sheath and said screens including injecting means for injecting at least one dose of a predetermined amount of a volatile liquid directly into the interior of said sheath and onto said screens so as to prevent excessive and insufficient moistening of said sheath and said screens.

2. A psychrometer according to claim 1; wherein said injecting means injects successive doses of said predetermined amount of liquid, at intervals, into the interior of said sheath and onto said screens, and said intervals between the injection of sucessive doses are sufficiently short for said sheath to never completely dry and sufficiently long for a steady psychrometric temperature to be measured by said second sensor means.

3. A psychrometer according to claim 1; further comprising memory means for receiving information calculated from the respective temperatures sensed by said first and second sensor means and a control device receiving a wet temperature signal from said second sensor means for calculating a temperature differential with respect to time of said wet temperature signal and for supplying an information recording command to said memory means when the value of said temperature differential falls below a predetermined level.

4. A psychrometer for measuring the water content in a flow of gas, comprising:
   suppport means;
   first sensor means mounted on said support means and located directly in said flow of gas for measuring the dry temperature of said flow of gas;
   second sensor means mounted on said support means for measuring the wet temperature of said flow of gas;
   a sheath surrounding said second sensor means and located in said flow of gas, said sheath being adapted to absorb a volatile liquid;
   a pair of screens mounted on opposite sides of said second sensor means and said sheath for protecting said sheath against thermal radiation;
   first wetting means for moistening each of said screens with a volatile liquid; and
   second wetting means for feeding said volatile liquid to said sheath including means for emitting said liquid in the form of at least one jet from an outlet orifice, a guide wall for receiving said at least one jet, and mounting means for mounting said guide wall at an upper end of said sheath and spaced from said outlet orifice so as not to intersect a vertical plane passing through said orifice.

5. A psychrometer according to claim 4; further comprising second mounting means for mounting said sheath at an angle which is inclined with respect to the horizontal, said sheath having a tubular configuration and an opening at the upper end thereof which receives said liquid supplied in the form of said at least one jet.

6. A psychrometer according to claim 5; wherein said tubular sheath is centered about an axis inclined at angle within the range of 20° to 60° with respect to the horizontal.

7. A psychrometer for measuring the water content in a flow of gas, comprising:
   support means;
   first sensor means mounted on said support means and located directly in said flow of gas for measuring the dry temperature of said flow of gas;
   second sensor means mounted on said support means for measuring the wet temperature of said flow of gas;
   a sheath surrounding said second sensor means and located in said flow of gas, said sheath being adapted to absorb a volatile liquid;
   a pair of screens mounted on opposite sides of said second sensor means and said sheath for protecting said sheath against thermal radiation;
   first wetting means for moistening each of said screens with a volatile liquid;
   second wetting means for feeding said volatile liquid to said sheath;
   mounting means for mounting said sheath including a sheath-carrier having a first tubular portion surrounding said sheath and supporting said sheath at an upper end thereof and a second portion supporting said first portion;
   means for detachably mounting said second portion on said support means; and
   channelling means for housing said first and second sensor means and through which said gas flows, wherein said second portion is detachable from said support means from outside of said channelling means.

* * * * *